United States Patent [19]
Varde et al.

[11] Patent Number: 5,106,296
[45] Date of Patent: Apr. 21, 1992

[54] METHOD AND DEVICE FOR DEFINING DIFFERENT JAW POSITIONS

[75] Inventors: Per Varde, Lidköping; Carl-Arne Andersson, Trollhättan, both of Sweden

[73] Assignee: Margareta Varde, Lidköping, Sweden

[21] Appl. No.: 377,843

[22] PCT Filed: Oct. 24, 1988

[86] PCT No.: PCT/SE88/00563
§ 371 Date: Jun. 22, 1989
§ 102(e) Date: Jun. 22, 1989

[87] PCT Pub. No.: WO89/03662
PCT Pub. Date: May 5, 1989

[30] Foreign Application Priority Data
Oct. 23, 1987 [SE] Sweden ............... 8704140-6

[51] Int. Cl.⁵ ............................................. A61C 11/00
[52] U.S. Cl. ........................................ 433/54; 433/60; 433/71; 433/75
[58] Field of Search ............... 433/44, 50, 54, 55, 433/56, 60, 68, 213, 61, 75, 71; 33/513, 514, 606

[56] References Cited
U.S. PATENT DOCUMENTS

| | | | |
|---|---|---|---|
| 2,386,103 | 10/1945 | Galley | 433/68 |
| 2,540,555 | 2/1951 | Slaughter, Jr. | 33/513 |
| 2,754,588 | 7/1956 | Cordell | 433/60 |
| 3,510,947 | 5/1970 | Tuccillo et al. | 433/60 |
| 4,319,875 | 3/1982 | Beckwith | 433/60 |

FOREIGN PATENT DOCUMENTS

| | | | |
|---|---|---|---|
| 505417 | 8/1954 | Canada | 433/56 |
| 3202997 | 7/1983 | Fed. Rep. of Germany | 433/54 |

Primary Examiner—Cary E. Stone

[57] ABSTRACT

Method for fixation of different positions of a model (2) of the mandible relatively to a model (1) of the maxilla of a patient. One of the models consists of two members (15, 16) namely a tooth member and a socket member unified along coinsiding joint surfaces forming a common boarder plane (19) in a predetermined mutual position. The method comprises impressions of the teeth of the mandible and maxilla respectively are made in an index (54) in the shape of a plastically deformable plate, partly in a thick plate and partly in a thin plate. The mandible and maxilla models (2) are positioned in an articulator (5) so that they coinside with the thick index. The thick index is replaced with the thin index, forming an interspace between the joint surfaces of the divided model. The interspace is cast by filling the space with a cast mass, obtaining a removable interlayer plate. The maxilla and the mandible models (1, 2) are fixed within the articulator in two positions, where one position is determined by the fact that the interlayer plate is positioned between the joint surfaces and the other position is determined by the fact that the joint surfaces contact each other without interlayer plate. The invention also relates to a device for the accomplishment of the method.

5 Claims, 9 Drawing Sheets

METHOD AND DEVICE FOR DEFINING DIFFERENT JAW POSITIONS

TECHNICAL FIELD

The present invention relates to a method for definition of different positions of a model of the lower jaw relatively to a model of the upper jaw according to the preamble of the accompanying claim 1.

The present invention relates to a device for the accomplishment of the method according to the preamble of the accompanying claim 6.

BACKGROUND

In connection with production of dental works there is sometimes required an orientation of the lower jaw model to the upper jaw model in one or several positions. By mounting the models within an articulator one aims at simulating the patients positions of the under jaw relatively to the upper jaw. By artificial jaw condyles the models are brought into different positions relatively to each other. To completely reproduce the motion pattern of the patient in this way is very difficult, as the anatomy is individual.

By means of wax bite a good orientation of the model can be accomplished. In connection with some dental works, such as bridges and positioners, the teeth are changed as to shape and/or positions so that the orientation of the upper jaw and the lower jaw models must freely be transferred to other media, usually articulator with artificial jaw condyles.

It is easy to mount the models in an articulator so they take one single position. In connection with production of bridges and positioners there are required several positions. To reproduce these positions in connection with artificial jaw condyles is complicated and nonexact.

The Object of the Present Invention

The object of the present invention is to accomplish a method and a device which facilitate reproduction of different positions between upper jaw and lower jaw models.

The Present Invention

Said object is achieved by means of the method according to the present invention the characteristics of which are apparent from the accompanying claim 1 and 6 respectively.

The method according to the present invention can be summarized so, that one in a divided lower jaw model (so called split cast) pushes in an individually shaped plaster plate (wafer). The under jaw can take different positions with respectively without wafer. Further positions can be taken by means of further wafers.

The method according to the present invention is developed for the production of positioners, but can be utilized also in connection with analysis of bite motions and production of bridge works. The method involves good possibilities for checks.

BRIEF DESCRIPTION OF THE DRAWINGS

The present invention will in the following be described in an embodiment with reference to the enclosed drawings, in which.

PREFERRED EMBODIMENTS

Figure 1:
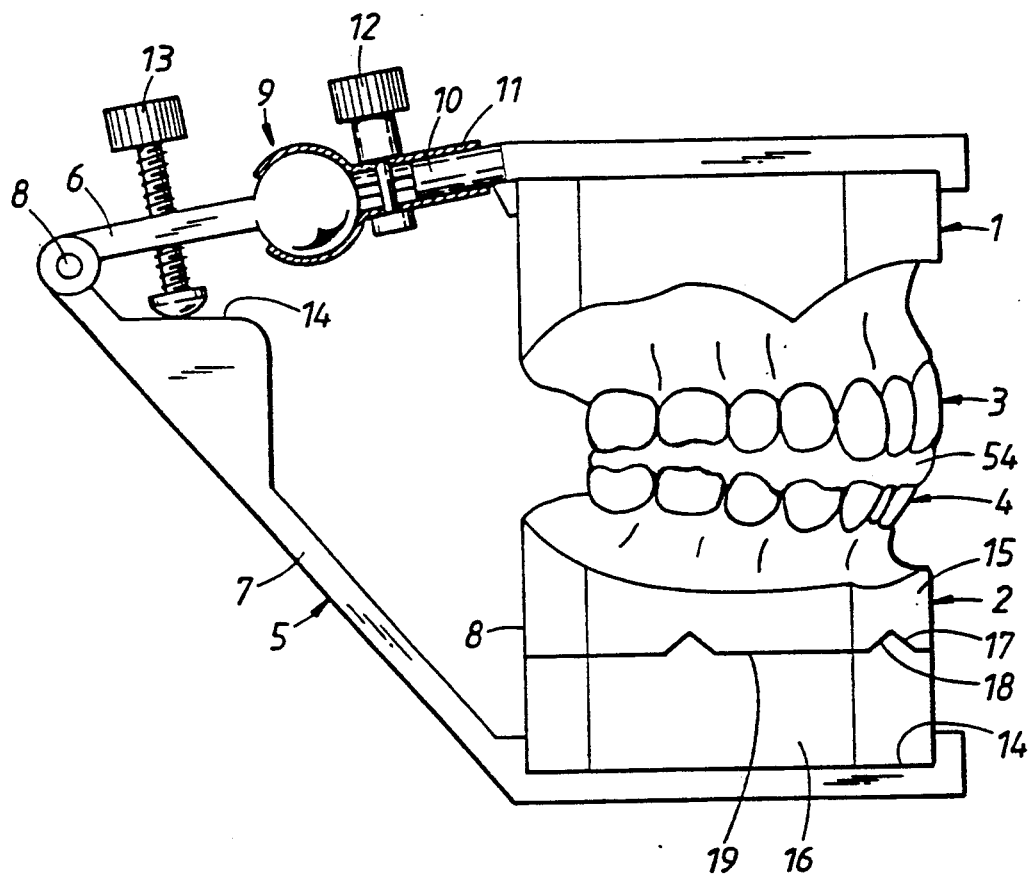
FIG. 1 shows an upper jaw model and an under jaw model in a completely schematically shown articulator in connection with the use of the method according to the invention.

In FIG. 1 an upper jaw model 1 and a lower jaw model 2 are shown, which models constitute castings of upper and lower toothed arches 3, 4 of a human being.

In order to study and fix positions of the upper jaw and bottom jaw models and then analyze bite potions and toothed positions of a person and produce dental works the upper jaw and lower jaw model 1, 2 are mounted into an articulator 5, which is schematically shown in FIG. 1. The articulator is per se well known for a man skilled in the art and should therefore not require any detailed description. For the present object it is sufficient to state that the articulator 5 consists of two relative to each other movable main parts 6, 7, which are pivotally journalled relatively to each other in a pivot 8 and that the upper jaw model is adjustable in all planes so that it by means of wax bite fits to the under jaw model. This is shown completely schematically in FIG. 1 by means of a ball pivot, a bar 10 extending in a tube 11 and a locking screw 12.

An adjustable stop screw 13 is attached on one of the pivot arms 6. In co-operation with a stop surface 14 positioned on the other pivot arm 7 an end position is hereby defined for the mutual relationship of the two pivot arm 6, 7, that is to say a least mutual angle between the pivot arms, corresponding to a certain interspace between the toothed arches 3, 4 which further will be described below.

Figure 2:
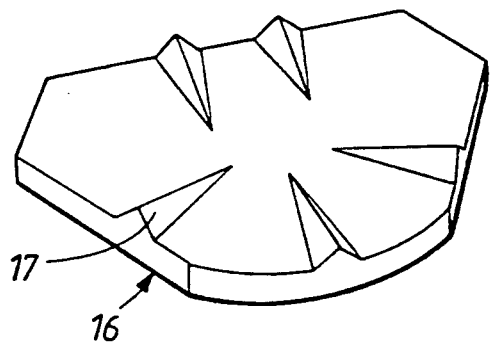
FIG. 2 shows a bottom plate, which forms a bottom part of the under jaw model.

Which is apparent from FIG. 1 one of the jaw models, in the shown example the lower jaw model, is divided into two portions 15, 16. One of the portions supports: the toothed arch 4 in the model and the other portion consists of a base portion 16 for the upper jaw model. The portions 15, 16 can be separated from each other and are provided with mutually cooperating positioning means 17, 18 in order to maintain correct relative positions between the two portions 15, 16. The positioning means consist of projections 17 and recesses 18 respectively which form deviations from planar border surfaces 19, which in the connected condition of the lower jaw model 2 are in contact with each other. In the shown example the under portion 16 is provided with the projections 17 whereas the upper portion 15 is provided with said recesses 18 having a shape which completely corresponds to the projections, but constitutes their negative equivalence and are consequently concave. The projections are arranged as wedge shaped portions having a shape which is shown in FIG. 2 in an example. This figure shows the under portion 16 of the under jaw model 2, but shows a somewhat different embodiment with respect to proportions and positioning of the projections.

The following description relates to production of positioners with reference to FIG. 4-8, in which the two pivot arms 6, 7 and pivot 8 of the articulator merely are shown by means of a dotted and dashed line and a point respectively. Two wax bites 54 are taken. One in bite position (intercuspidation position IP) and one in that position which the under jaw will take when the positioner is positioned (construction position CP). The models are mounted by means of the CP wax bite 54 in the articulator, see FIG. 1. The under jaw model is split (split cast) in parallel with the chewing plane of the teeth. The model portion containing teeth is removed so that it fits the IP wax bite. A gap width is formed between the model portions. This gap width is filled with plaster and forms after the solidification an interlayer plate (wafer), see FIG. 4 and 6. This interlayer wafer 50 constitutes a representation of the interspace between the upper and the lower portion 15, 16 of the lower jaw model. The upper side of the plate achieves consequently the projection 51, whereas the underside achieves recesses 52 with a position corresponding to the position of corresponding recesses 17 respectively projections of the border surfaces 19 of the two portions 15, 16. As is apparent from FIG. 6 a possible displacement sidewards in the jaw relations is illustrated by means of a lateral displacement of the projections 51 relative to the recesses 52 studied from the rear plane 8 of the under jaw model 2. The under jaw can easily take two positions, one with wafer corresponding to the IP wax bite and another without wafer corresponding to the CP position.

Figure 3:
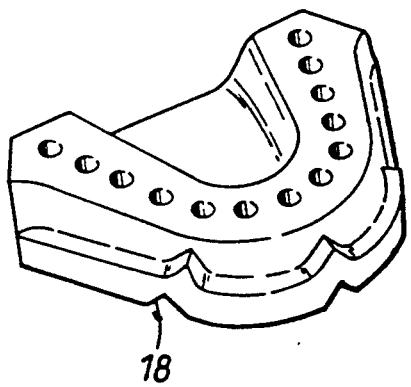
FIG. 3 shows a so called set-up model.
Figure 4:
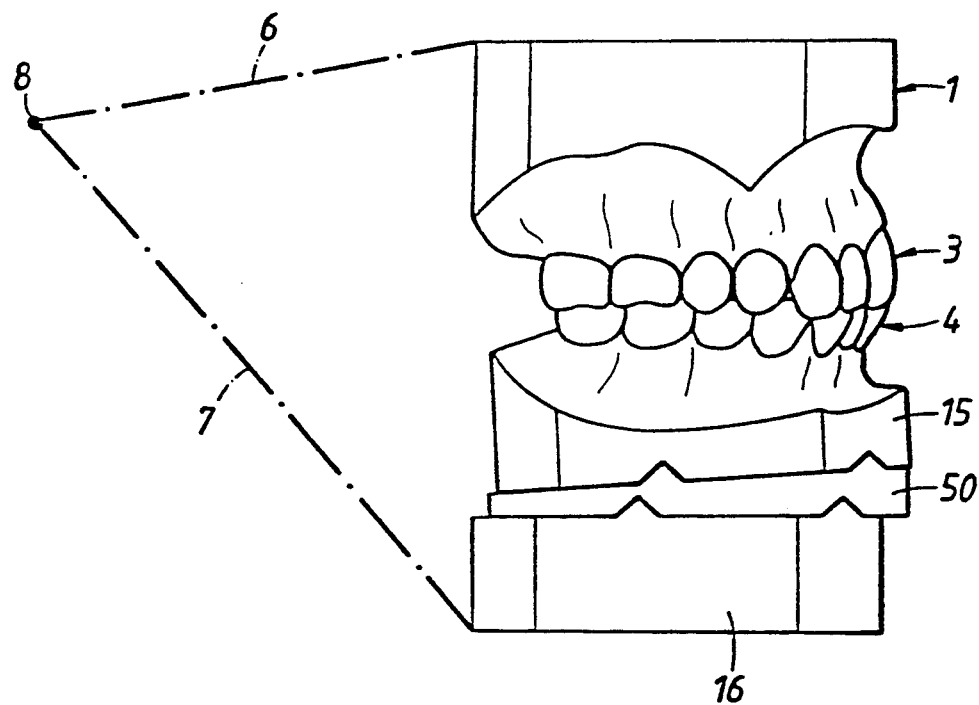
FIG. 4 shows the jaw models in a closed position in the articulator.
Figure 5:
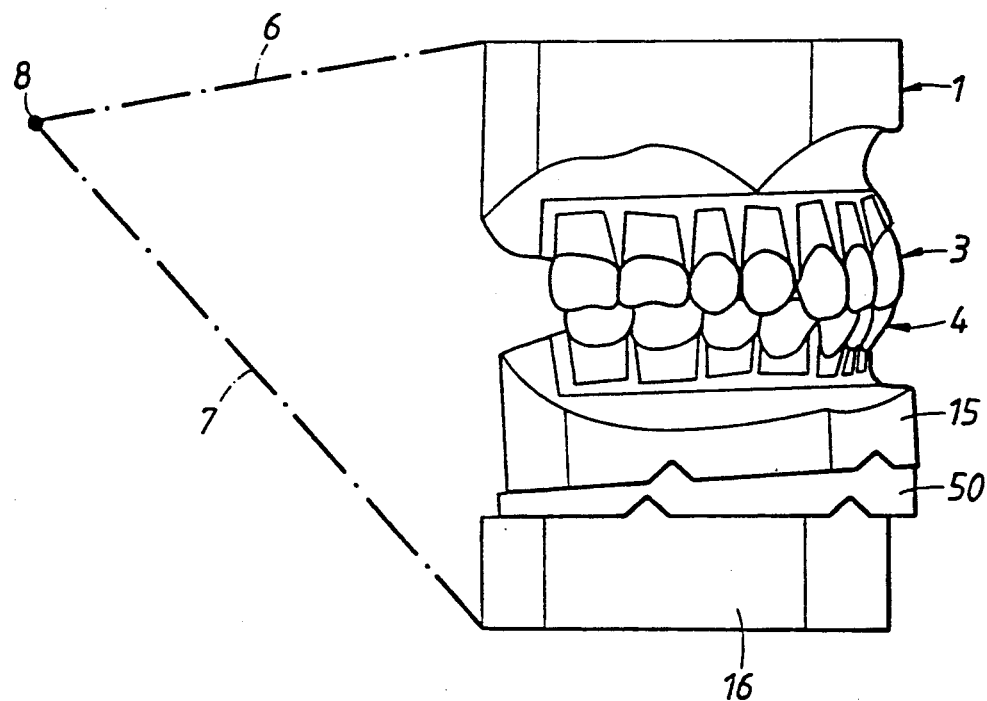
FIG. 5 shows the set-up model in a closed position in the articulator and FIG. 6 shows a view of the rear plane of an interlayer plate formed by means of the method according to the present invention.
Figure 6:
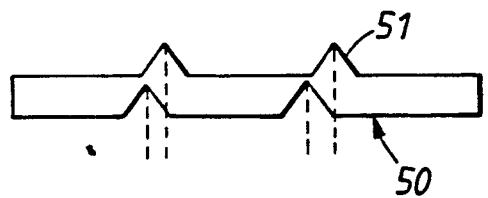
Figure 7:
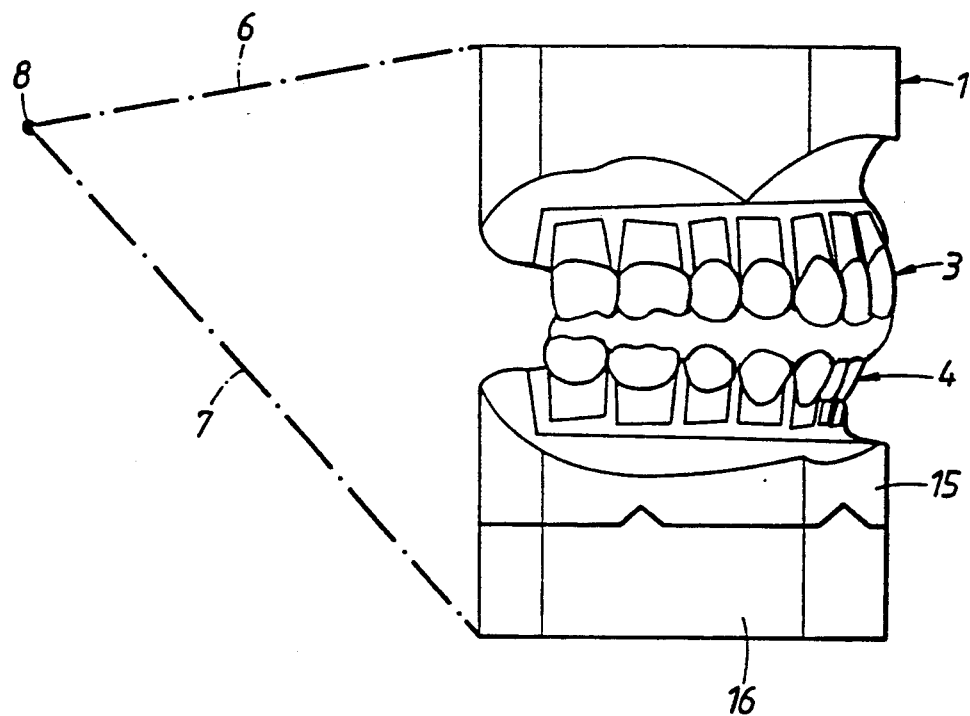
FIG. 7 shows the set-up model having the interlayer plate removed and the interspace between the toothed arches filled with wax and FIG. 8 shows the wax impression positioned between the jaw models of a duplicate of the set-up model.
Figure 8:
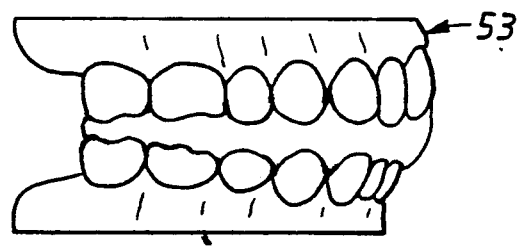

Said models are utilized as a reference and are here denominated the study model. One can check the displacement of the under jaw from IP to CP by studying the projections and thickness of the wafer. On the duplicate model the model is sawn so that each tooth will be separated from the other ones. On a especially produced model base in split cast embodiment for the under jaw, the teeth are set up in wax. An example of such set-up model is shown in FIG. 3. This one has a shape on its underside with a planar border surface and recesses 18 which fit to the projections and the border surface of the under portion 16 of the under jaw model shown in FIG. 2. One provides for that the distance from the chewing plane to the gap is the same as on the study model. The teeth are set up in position corresponding to the IP wax bite, that is to say with wafer, see FIG. 5. The same wafer as for the study models is utilized.

The teeth are set up in a good intercuspidation according to instructions from the dentist. The wafer is removed and then a gap is formed between the teeth of the upper jaw and the under jaw. This gap is filled with wax. After cutting the wax bite one checks that the wax bite fits, that is to say no gap must arise between the model base and the bottom plate. The split cast model provides for a very good possibility for checks. The produced wax bite is utilized for the production of positioners in a usual manner, utilizing a special duplicate of the set-up model which is shown by means of an example in FIG. 8.

For exact fit between the bottom plate and the model base and the study model respectively one proceeds in the following manner.

The bottom plate is cast in a special mould. Thereafter the model base is cast with the bottom plate as a counter cast mould. The same bottom plate is utilized as a counter cast mould for the study model. The wafer which is produced with a bottom plate and the study model as a counter cast mould will therefore also fit the model base.

Figure 9:
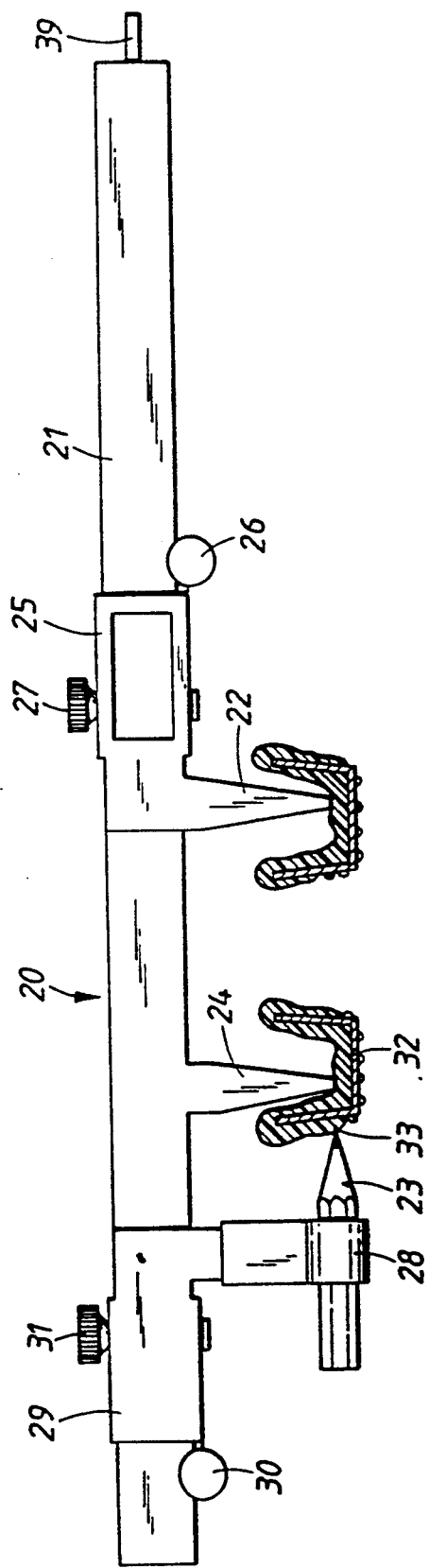
FIG. 9 shows a measuring tooth for the use in connection with the production of jaw models.
Figure 10:
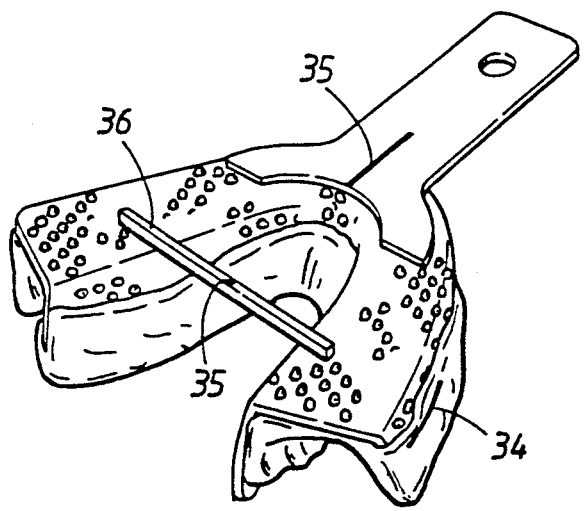
FIG. 10 shows an impression of a toothed arch and FIG. 11 shows the use of the measuring tool for measuring in connection with casting the impression.
Figure 11:
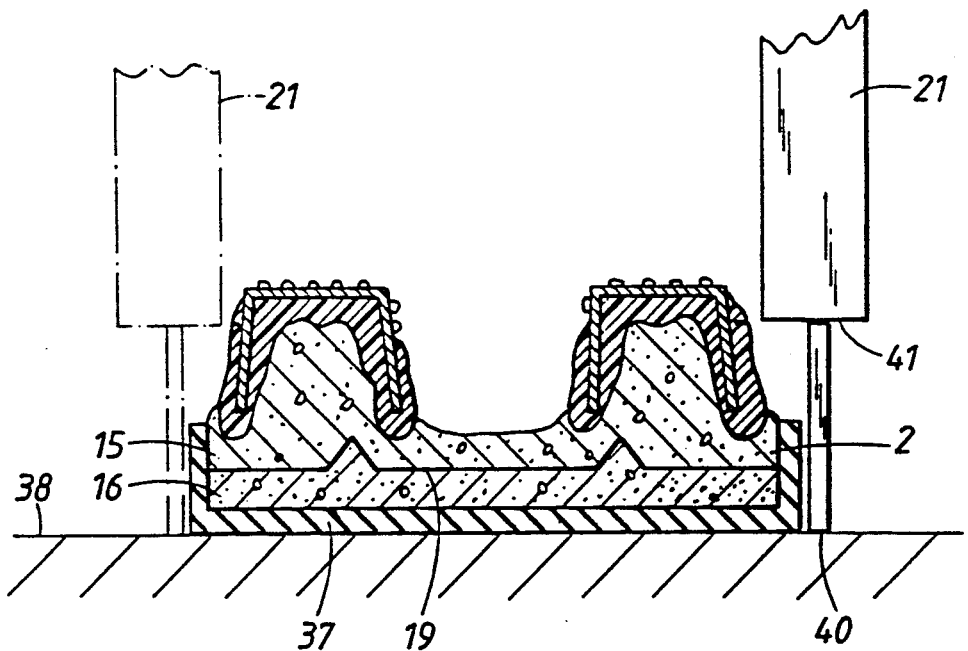

With reference to FIG. 9, 10 and 11 a measuring instrument and its use will be described in connection with the production of plaster models. The measuring tool 20 has an embodiment, which is partly similar to a sliding caliper having a bar 21, along which a peg 22 and a pen 23 are displaceable and lockable to the bar in predetermined positions. A further peg 24 is fixed to the bar. The movable peg 22 projects from a slide 25 which is displaceable along the bar by means of a set screw 26 which is rotatably connected to the slide 25 and by means of its contact with the bar displaces the slide along the same. A set position can be locked by means of a locking screw 27. The pen 23 is positioned in a holder 28, which in a corresponding manner as the movable peg 22 is supported by the slide 29 with a set screw 30 and a locking screw 31. After impressions 32 having been taken by the toothed arch one of the pegs 22 is inserted into the impression of a tooth on one side, whereas the other peg 24 is brought down into the corresponding impression on the other side. The distance between the pegs is adjusted by means of rotating the set screw 26 so that the pegs fit into the impression. The pen 23 is pushed so that a mark 33 is indicated on the outside of the impression 32. The measuring tool is turned so that a mark is indicated in a corresponding manner on the other side of the impression. The procedure is repeated on impressions of teeth further forward in the mouth. Consequently one achieves two marks on each side of the impression. These marks are connected by means of a line 34 which constitutes the chewing plane. Also the central line 35 is marked. In the rear area the central line can be marked on a bridging pin 36, connected by means of wax, such as a match or similar. When ejecting the impression of a plaster in a rubber mould 37, see FIG. 11, there is checked that both lateral lines are at the same height from the border plane 19 between the two portions 15, 16 in the split cast model 2 and consequently also from the bottom plane. This is checked by checking the height from a support plane 38, on which the rubber mould rests. This is checked by means of the measuring tool, which similar to a conventional slide caliper has a rod 39, which is movable relative to the bar 21 and is connected to the slide 25. It is apparent from FIG. 11 that the measurement is accomplished by setting the end 40 of the rod 39 against the support plane 38 and adjusting the end edge 41 of the bar at a height corresponding to the line on one of the sides and checking against the position of the line on the other side. The central line 35 is checked so that it is perpendicular to the rear plane of the rubber mould. In this way one achieves a model 2 of one of the jaws, where the base plane is parallel to the chewing plane of the teeth and the rear plane is perpendicular to the central line of the toothed arch.

It is suitable that the border plane is made parallel to the chewing plane. When the border plane is made by means of split cast relief the border plane cannot be ground which is usually done with the base plane of study models. If one would have a slight inclination between the border plane and the chewing surface, one has to provide for a corresponding inclination also on the set-up model. In either case one does not obtain the same displacement of position of the chewing plane of the study model as of the chewing plane of the set-up model, when one shifts between position with and without wafer respectively. One also provides for that the teeth of the set-up model have the same horizontal relation to the position means as of the study models.

Figure 12:
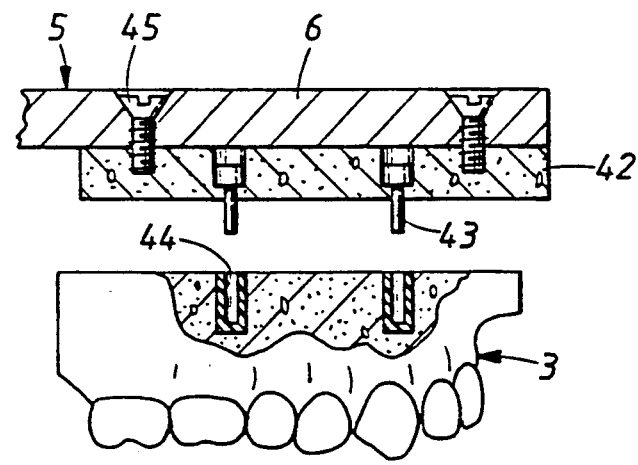
FIG. 12 shows a partly broken view through a connection device for jaw models into the articulator.
Figure 12:
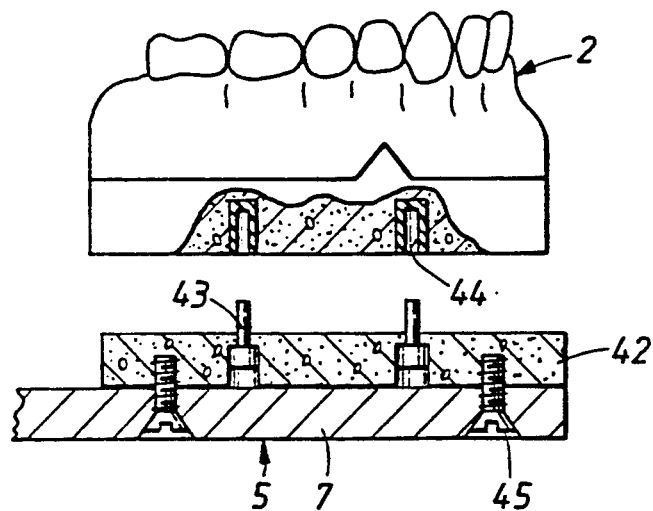
Figure 13:
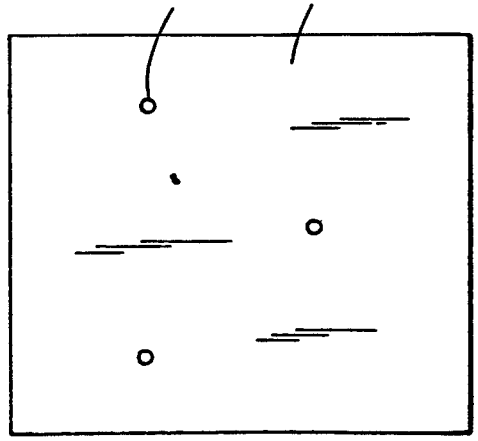
FIG. 13 shows a planar view over a part of the articulator.

Instead of connecting plaster models either by means of connecting by means of a plaster or by means of screwing the models from the side as a screw vice, one can preferably, as shown in FIG. 12 and 13, utilize a special connecting device 41 for each jaw model 1, 2 and connecting means in the shape of a number of pins 43 and holes 44. The plate 42 is screwed tight by means of screws 45 in the present pivot arms 16, 17 of the articulator 5. The pins are for example three in number and positioned in the corners of a triangle with standardized distances between the pins. The holes 44 are positioned in each jaw model 1, 2 respectively with positions and dimensions such, that the pins with a certain friction can be inserted into the holes and hold the jaw models fixed to the articulator.

From FIG. 13 examples of the position of the pins in the plate 42 are apparent.

Figure 14:
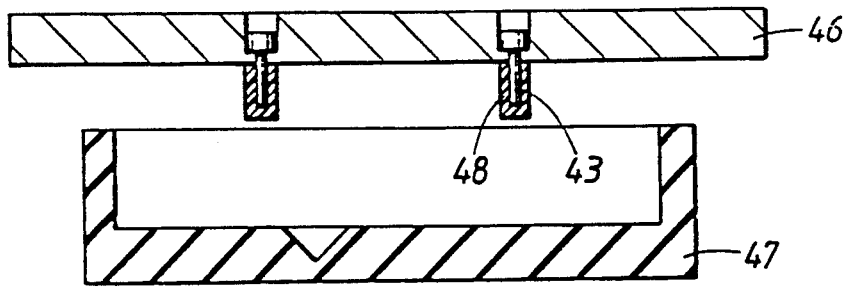
FIG. 14 and 15 shows schematically the preparation of the connection device.
Figure 15:
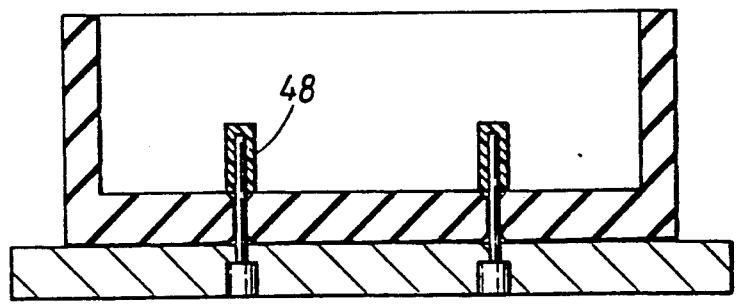

In FIGS. 14 and 15 an example of a production of the holes 44 is shown. The holes of the lower jaw model or more in detail its base portion are obtained by that a cover 46 to the mould 47 for one portion 16 of the lower jaw model, namely the base portion, is provided with pins 43. Tubes 48 made by plastics or similar are third on said pins, whereafter the tubes are cast in the plaster in connection with ejection of the impression. When the model as achieved has been taken away from the rubber mould 47, three holes are obtained in the base plane of the mould. Said holes fit to the bins of the plate 42 which is screwed onto the articulator 9. Plates provided with pins can be adapted and screwed onto articulators of different types. Only articulators, where the upper jaw part is adjustable relative to the lower jaw part can come in question as no plastering takes place.

By providing the articulator with plates with pins plaster base portions, cast with fitting holes, can be rapidly and firmly mounted in articulators.

The invention is not limited to the embodiments as described above and shown in the drawings, but can be modified within the frame of the accompanying claims. For example different connecting devices can be chosen for connecting the jaw models to the present articulator.

We claim:

1. A method for fixation of different positions of a model of the lower jaw relative to a model of the upper jaw of a patient, one of said models including two portions, namely a tooth portion and base portion, joined along coinciding joint surfaces, forming a common border plane in a predetermined relative position, comprising the following steps;

making impressions of the upper jaw and lower jaw teeth both in a thicker bite plate and in a thinner bite plate, said plates being placed in a plastically deformable material to make said impressions;

positioning the lower and upper jaw models in an articulator so that they coincide with the thicker bit plate;

replacing the thicker bit plate with the thinner one, forming an interspace between the joining surfaces of the said one model;

casting said interspace by filling the interspace with a cast compound, obtaining a removable interlayer plate; and fixating said upper jaw and lower jaw models in the articulator in two positions, where one position is determined by the interlayer plate being positioned between the joint surfaces and the other position is determined by the joint surfaces contacting each other without an interlayer plate.

2. A method according to claim 1, wherein, that at least two bite plates are provided for by means of plastically deformable plates of a relatively different thickness, said different bite plates being positioned one at a time into the articulator, obtaining different large interspaces between the portions of the divided jaw model, and making a casting of said interspace for each bite member.

3. A method according to claim 1, wherein the jaw models are produced both as a reference model and in the shape of a corrected model, of which the teeth are corrected to desired relative positions and/or shape, utilizing moulds for the production of two-part split models, wherein, the mould is arranged to provide the base portion with a relief forming positioning means, which form counter moulds against the reference model as well as the corrected model.

4. A method according to claim 3, wherein the divided reference model is produced within a mould with the chewing plane parallel to the border plane of the two-part split model, further comprising, that the depth of the impressions is marked at at least four places, indicating the chewing plane of the teeth, whereafter during the production of the model in the mould all markings are positioned at a relatively same distance from a chosen reference plane and checked for such positioning, by comparison of the distance from said reference plane to the markings in each place whereby the chewing plane of the models remain parallel with the border plane of the two-part split models.

5. A method according to claim 4, further comprising marking a symmetrical line in the shape of a central line on the outside of the impression, and providing a straight line relative to the rear plane of the mould and consequently the present jaw model for said central line of both of the jaw models form during the casting.

* * * * *